United States Patent [19]

Müller et al.

[11] Patent Number: 5,741,937
[45] Date of Patent: Apr. 21, 1998

[54] PROCESS FOR THE PREPARATION OF ARYLIDENE-SUBSTITUTED ALKYLCYCLOALKANONES

[75] Inventors: Nikolaus Müller, Monheim; Thomas Essert, Overath, both of Germany

[73] Assignee: Bayer Aktiengesellschaft, Leverkusen, Germany

[21] Appl. No.: 668,402

[22] Filed: Jun. 21, 1996

[30] Foreign Application Priority Data

Jun. 28, 1995 [DE] Germany ............... 195 23 450.2

[51] Int. Cl.$^6$ ........................................ C07C 45/45
[52] U.S. Cl. ........................... 568/312; 568/313
[58] Field of Search ........................ 568/312, 313

[56] References Cited

U.S. PATENT DOCUMENTS 3,400,101  9/1968  Elam et al. ................... 568/313
4,118,558  10/1978  Turk et al. ................... 568/313
4,182,729  1/1980  Collins ........................ 568/313
4,271,319  6/1981  Tang et al. ................... 568/313
4,908,481  3/1990  Hoffmann et al. ............ 568/313

FOREIGN PATENT DOCUMENTS 43 20 498 A1  12/1994  Germany ................... 568/313

OTHER PUBLICATIONS

W.S. Johnson, J.Am.Chem.Soc., vol. 65, pp. 1317–1324 (1943).

*Primary Examiner*—James H. Reamer
*Attorney, Agent, or Firm*—Sprung Kramer Schaefer & Briscoe

[57] ABSTRACT

Arylidene-substituted alkylcycloalkanones are prepared from alkyl-substituted cycloalkanones by reaction with aromatic carbonyl compounds in the presence of a basic catalyst and water.

9 Claims, No Drawings

PROCESS FOR THE PREPARATION OF ARYLIDENE-SUBSTITUTED ALKYLCYCLOALKANONES

The present invention relates to a particularly advantageous process for the preparation of arylidene-substituted alkylcycloalkanones by condensation of alkylcycloalkanones with aromatic aldehydes or aralkyl ketones.

It is known that spiro-[2.4]-heptan-4-one can be reacted with 4-chlorobenzaldehyde in methanolic sodium hydoxide solution to give 5-(4-chlorobenzylidene)spiro[2.4]-heptan-4-one (see DE-A 43 20 498, Example 1). A disadvantage is the extremely long reaction time required, of 50 hours.

It is also known to react 2-methylcyclohexanone with benzaldehyde in the presence of a solution of sodium hydroxide in a mixture of 37.5% by volume alcohol and 62% by volume water. In this way, it is possible over the course of 3 hours to obtain, in a yield of from 65 to 70%, 2-benzal-6-methylcyclohexanone (=2-methyl-6-benzylidenecyclohexanone (see J. Am. Chem. Soc. 65, 1317 (1943)). Disadvantages are the relatively low yield and the fact that the product is obtained as an oil which must be extracted and worked up by distillation.

There therefore continues to be a need for a process by means of which arylidene-substituted alkylcycloalkanones can be prepared with high yields, in short reaction times and without complex working up.

A process for the preparation of arylidene-substituted alkylcycloalkanones of the formula (I)

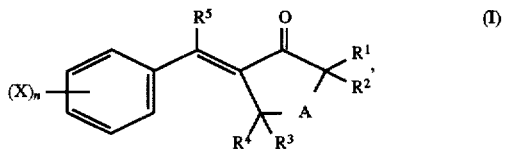

in which
- A represents optionally substituted —(CH$_2$)—$_x$ where x=1, 2 or 3,
- R$^1$ and R$^2$ represent identical or different optionally substituted C$_1$–C$_4$-alkyl or C$_3$–C$_7$-cycloalkyl radicals, or R$^1$ and R$^2$, together with the carbon atom between them, form a C$_3$–C$_7$-cycloalkyl radical,
- R$^3$, R$^4$ and R$^5$ are identical or different and represent hydrogen or optionally substituted C$_1$–C$_4$-alkyl or C$_3$–C$_7$-cycloalkyl, it also being possible for R$^3$ and R$^4$, together with the carbon atom between them, to form a C$_3$–C$_7$-cycloalkyl radical,
- X represents halogen, cyano, nitro, C$_1$–C$_4$-alkyl, C$_1$–C$_4$-halogenoalkyl, C$_1$–C$_4$-alkoxy or C$_1$–C$_4$-halogenoalkoxy, and where two or more radicals X are present they may be identical or different, and
- n represents zero or an integer from 1 to 5, has now been found, which is characterized in that substituted cycloalkanones of the formula (II)

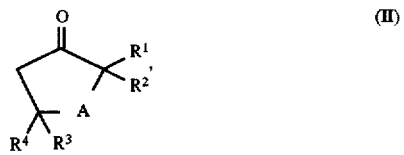

in which
the symbols used have the meaning given for formula (I), are reacted with aromatic carbonyl compounds of the formula (III)

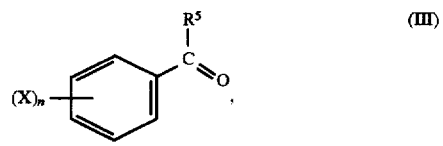

in which
the symbols used have the meaning given for formula (I), in the presence of a basic catalyst and water.

A can optionally contain one or more identical or different substituents from the group consisting of C$_1$–C$_4$-alkyl and C$_3$–C$_7$-cycloalkyl, where C$_1$–C$_4$-alkyl can in turn optionally be substituted by halogen or C$_1$–C$_4$-alkoxy, and C$_3$–C$_7$-cycloalkyl can in turn optionally be substituted by halogen, C$_1$–C$_4$-alkyl or C$_1$–C$_4$-alkoxy. A preferably represents —CH$_2$—, —CH$_2$—CH$_2$— or —CH$_2$—CH$_2$—CH$_2$—, i.e. 2-alkyl- or 2,2-dialkyl-cyclopentanones, -cyclohexanones or -cycloheptanones of the formula (II) are preferably reacted with substituted benzaldehydes of the formula (III) to give 2-alkyl- or to give 2,2-dialkyl-5-arylidene-cyclopentanones, to give 2-alkyl- or to give 2,2-dialkyl-6-arylidene-cyclohexanones or to give 2-alkyl- or to give 2,2-dialkyl-7-arylidene-cycloheptanones of the formula (I).

Where R$^1$ and R$^2$ represent C$_1$–C$_4$-alkyl, this radical can optionally be substituted by halogen, C$_1$–C$_4$-alkoxy, halogeno-C$_1$–C$_4$-alkoxy, C$_2$–C$_4$-alkenyl, C$_2$–C$_4$-alkinyl, halogeno-C$_2$–C$_4$-alkenyl or halogeno-C$_2$–C$_4$-alkinyl. Where R$^1$ and R$^2$ represent C$_3$–C$_7$-cycloalkyl, this radical can be substituted by halogen, C$_1$–C$_4$-alkoxy or C$_1$–C$_4$-alkyl. R$^1$ and R$^2$ independently of one another preferably represent unsubstituted C$_1$–C$_4$-alkyl or unsubstituted C$_3$–C$_4$-alkenyl.

Where R$^3$, R$^4$ and R$^5$ represent C$_1$–C$_4$-alkyl, this radical can optionally be substituted by halogen or C$_1$–C$_4$-alkoxy. Where R$^3$ and R$^4$ represent C$_3$–C$_7$-cycloalkyl, this radical can optionally be substituted by halogen, C$_1$–C$_4$-alkyl or C$_1$–C$_4$-alkoxy. R$^3$, R$^4$ and R$^5$ preferably represent hydrogen.

X preferably represents fluorine, chlorine, cyano or C$_1$–C$_4$-alkyl.

n preferably represents zero, 1 or 2. When n=1, X is preferably in position 4. When n=2, X is preferably in positions 2 and 4.

Particularly preferred starting materials of the formula (II) are 2-methylcyclopentanone, 2,2-dimethylcyclopentanone, 2-ethylcyclopentanone, 2,2-diethylcyclopentanone, 2-isopropylcyclopentanone, 2-methylcyclohexanone and 2-methylcycloheptanone.

Particularly preferred compounds of the formula (III) are: 4-chlorobenzaldehyde, 4-fluorobenzaldehyde, 4-methoxybenzaldehyde, 4-methylbenzaldehyde and 2,4-dichlorobenzaldehyde.

As basic catalysts it is possible, for example, to employ alkali and alkaline earth metal hydroxides, such as lithium hydroxide, sodium hydroxide, potassium hydroxide, caesium hydroxide, magnesium hydroxide, calcium hydroxide, strontium hydroxide and barium hydroxide, and alkali metal and alkaline earth metal carbonates, such as sodium carbonate, potassium carbonate, calcium carbonate and magnesium carbonate, and oxides of the said elements which form hydroxides or carbonates under the reaction conditions.

Preferred basic catalysts are sodium hydroxide, potassium hydroxide, magnesium hydroxide, calcium hydroxide, sodium carbonate and potassium carbonate. Sodium hydroxide and potassium hydroxide are particularly preferred.

It is an essential feature of the present invention that the reaction medium employed is water. The reaction medium can optionally contain up to 20% by volume, preferably up to 10% by volume and in particular up to 5% by volume, of organic solvents, for example alcohols such as methanol, ethanol, n-propanol, isopropanol and butanols, sulphones, such as dimethyl sulphoxide and tetramethylene sulphone, ethers, such as tetrahydrofuran, and amides, such as dimethyl-, diethyl-, di-n- and -isopropyl-, dibutyl-, dipentyl-, dihexyl-, dicyclohexylformamide, N-methylpyrrolidone, N-methylpiperidone, N-methylcaprolactam, and higher N-alkylpyrrolidines, -piperidones and -caprolactams.

Very particular preference is given to the use of water without additions of other solvents.

The process according to the invention can be carried out, for example, at temperatures from 20 to 200° C. Preferred temperatures are from 50° to 170° C., especially from 90 to 150° C. At temperatures above the boiling point of the reaction mixture it is necessary to carry out the reaction in a closed vessel at the autogenous pressure or at pressures of, for example, up to 10 bar.

The quantity of reaction medium employed can for example be between 100 and 1,000 ml per mole of compound of the formula (II) employed. This quantity is preferably from 300 to 700 ml, particularly preferably from 400 to 600 ml.

The starting materials of the formulae (II) and (III) are preferably employed in an equimolar ratio. Excesses of one or the other component are also possible, for example from 0.5 to 2 mol of the compound of the formula (II) per mole of the compound of the formula (III).

The ratio of catalyst to compound of the formula (II) can for example be from 0.02 to 0.2 equivalent per mole. Preference is given to from 0.05 to 0.1, in particular from 0.07 to 0.09, equivalent of catalyst per mole of the compound of the formula (II).

The reaction mixture obtained after carrying out the process according to the invention can be worked up very simply, for example by cooling it to room temperature, for example, and filtering off the solid which is present, washing it with water and drying it.

A preferred embodiment of the process according to the invention is explained below, taking as example the reaction of 2-methylcyclopentanone with 4-chlorobenzaldehyde in the presence of potassium hydroxide:

A solution of potassium hydroxide and water is charged to the reaction vessel, for example a pressure autoclave, and 2-methylcyclopentanone and 4-chlorobenzaldehyde are added. The mixture is heated to reaction temperature under the intrinsic pressure (at reaction temperatures below 100° C. it is also possible to operate without pressure) and allowed to react at this temperature for a certain time. After cooling to room temperature, the product which is crystallized out is filtered off with suction, washed with water and dried.

It is extremely surprising that the aldol condensation according to the invention can be carried out so easily in an aqueous medium with compounds of the formula (III) which are relatively insoluble in water. The yields which can be achieved are in general more than 85% of theory, frequently more than 90% of theory in the case of short reaction times.

It is additionally surprising that, despite the use of strongly alkaline catalysts, there are no notable losses in yield by Cannizzaro reactions. The process according to the invention enables the preparation of arylidene-substituted alkyl-cycloalkanones in high yields and can be carried out with great simplicity.

A particular advantage of the process according to the invention lies in the use of water as reaction medium, since the complex recycling of solvent is then unnecessary. The desired reaction products of the formula (I) can be separated and isolated in a simple manner. The possibility of working at relatively high temperatures leads to shorter reaction times, and consequently less by-products. The reaction time is frequently less than 14 hours, in particular from 2 to 11 hours.

The arylidene-substituted alkylcycloalkanones of the formula (I) which can be prepared by the process according to the invention are valuable intermediates for the production of pesticides, especially fungicides (see EP-A 378 953, EP-A 537 909 and EP-A 329 397).

EXAMPLES

Percentages are by weight unless stated otherwise.

Example 1

A solution of 16.8 g of 85% strength aqueous potassium hydroxide solution and 1,500 ml of water was charged to a 3 l stainless-steel autoclave, 294 g of 2-methylcyclopentanone and 421.8 g of 4-chlorobenzaldehyde were added, and the mixture was then heated to 120° C. under the intrinsic pressure. Stirring was subsequently carried out at this temperature for 3 hours. After cooling to room temperature, the finely particulate yellow product was filtered off with suction, washed to neutrality with water and then dried in a vacuum oven at 60° C. In this way 658.5 g of 2-methyl-5-(4-chlorobenzylidene)-cyclopentanone (93.1% pure) were obtained. This corresponds to a yield of 93% of theory.

Example 2

A solution of 2.8 g of 85% strength potassium hydroxide and 250 ml of water was charged to a stirred 3-necked flask apparatus with reflux condenser, 68 g of p-anisaldehyde and 49 g of 2-methylcyclopentanone were added, and the mixture was boiled under reflux for 3 hours. It was subsequently cooled to room temperature and the yellow solid which had crystallized out was filtered off with suction, washed to neutrality with water and dried in a vacuum oven at 60° C. In this way 98.3 g of 2-methyl-5-(4-methoxybenzylidene)-cyclopentanone (93.2% pure) were obtained. This corresponds to a yield of 85% of theory.

Example 3

A solution of 2.8 g of 85% strength aqueous potassium hydroxide solution and 250 ml of water was charged to a 0.7 l stainless-steel autoclave, and 49 g of 2-methylcyclopentanone and 68 g of p-anisaldehyde were added. The mixture was subsequently heated to 120° C. with stirring under the intrinsic pressure and subsequently stirred under the intrinsic pressure (1.5 bar) for 3 hours. After cooling to room temperature, the precipitated solid was filtered off with suction, washed to neutrality with water and dried in a vacuum oven at 55° C. In this way 101.5 g of 2-methyl-5-(4-methoxybenzylidene)-cyclopentanone (pure according to gas chromatography) were obtained. This corresponds to a yield of 94% of theory.

Example 4

The procedure of Example 3 was repeated but using 87.5 g of 2,4-dichlorobenzaldehyde instead of p-anisaldehyde. In this case, at 120° C. the reaction mixture had an intrinsic pressure of 1.2 bar. In this way 116 g of 2-methyl-5-(2,4-dichlorobenzylidene)-cyclopentanone (93.7% pure) were obtained. This corresponds to a yield of 85% of theory.

Example 5

A solution of 1.1 g of 85% strength aqueous potassium hydroxide solution and 100 ml of water was charged to a 0.31 stainless-steel autoclave, and then 25.2 g of 2-isopropylcyclopentanone and 28.1 g of 4-chlorobenzaldehyde were added, and the mixture was heated to 120° C. under the intrinsic pressure and subsequently stirred at this temperature (intrinsic pressure 1 bar) for 5 hours. After cooling to room temperature, the suspension was filtered with suction and the product was washed to neutrality with water and then dried in a vacuum oven at 55° C. In this way 46.8 g of 2-isopropyl-5-(4-chlorobenzylidene)-cyclopentanone (98.7% pure) were obtained. This corresponds to a yield of 93% of theory.

Example 6

A solution of 1.5 g of 85% strength aqueous potassium hydroxide solution in 135 ml of water was charged to a 0.31 stainless-steel autoclave, and then 47.5 g of 2,4-dichlorobenzaldehyde and 30.5 g of 2-methylcyclohexanone were added, and the mixture was subsequently heated to 150° C. under the intrinsic pressure (to 3.8 bar). Stirring was subsequently carried out at this temperature for 10 hours. After cooling to room temperature, the suspension was filtered with suction and the solid product was washed to neutrality with water and dried in a vacuum oven at 55° C. In this way 62.8 g of 2-methyl-6-(2,4-dichlorobenzylidene)-cyclohexanone (99.5% pure) were obtained. This corresponds to a yield of 86% of theory.

What is claimed is:

1. A process for the preparation of an arylidene-substituted alkylcycloalkanone of the formula

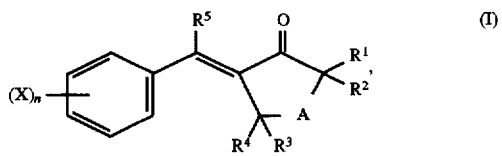

in which

A represents —(CH$_2$)—$_x$ where x=1, 2 or 3, which is unsubstituted or substituted with one or more identical or different substituents from the group consisting of C$_1$–C$_4$-alkyl and C$_3$–C$_7$-cycloalkyl, where C$_1$–C$_4$-alkyl can in turn optionally be substituted by halogen or C$_1$–C$_4$-alkoxy, and C$_3$–C$_7$-cycloalkyl can in turn optionally be substituted by halogen, C$_1$–C$_4$-alkyl or C$_1$–C$_4$-alkoxy, R$^1$ and R$^2$ represent identical or different C$_1$–C$_4$-alkyl or C$_3$–C$_7$-cycloalkyl radicals which are unsubstituted or substituted whereby C$_1$–C$_4$-alkyl can be substituted by halogen, C$_1$–C$_4$-alkoxy, halogeno-C$_1$–C$_4$-alkoxy, C$_2$–C$_4$-alkenyl, C$_2$–C$_4$alkinyl, halogeno-C$_2$–C$_4$-alkenyl or halogeno-C$_2$–C$_4$-alkinyl, and C$_3$–C$_7$-cycloalkyl can be substituted by halogen, C$_1$–C$_4$-alkoxy or C$_1$–C$_4$-alkyl, or R$^1$ and R$^2$, together with the carbon atom between them, form a C$_3$–C$_7$-cycloalkyl radical, R$^3$, R$^4$ and R$^5$ are identical or different and represent hydrogen, C$_1$–C$_4$-alkyl or C$_3$–C$_7$-cycloalkyl, which are unsubstituted or substsituted whereby C$_1$–C$_4$-alkyl can be substituted by halogen or C$_1$–C$_4$-alkoxy and C$_3$–C$_7$-cycloalkyl can be substituted by halogen, C$_1$–C$_4$-alkyl or C$_1$–C$_4$-alkoxy, it also being possible for R$^3$ and R$^4$, together with the carbon atom between them, to form a C$_3$–C$_7$-cycloalkyl radical.

X represents halogen, cyano, nitro, C$_1$–C$_4$-alkyl, C$_1$–C$_4$-halogenoalkyl, C$_1$–C$_4$-alkoxy or C$_1$–C$_4$-halogenoalkoxy, and where two or more radicals X are present they may be identical or different, and n represents zero or an integer from 1 to 5, in which a substituted cycloalkanone of the formula (II)

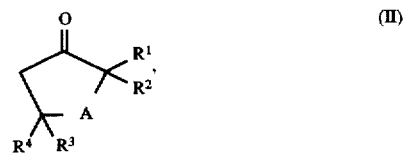

in which the symbols used have the meaning given for formula (I), are reacted with aromatic carbonyl compounds of the formula (III)

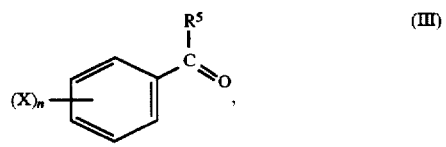

in which the symbols used have the meaning given for formula(I), in the presence of a basic catalyst, water and up to 20% by volume of organic solvents.

2. The process of claim 1, in which in the formulae R$^3$, R$^4$ and R$^5$ represent hydrogen, X represents fluorine, chlorine, cyano or C$_1$–C$_4$-alkyl, and n represents 0, 1 or 2.

3. The process of claim 1, in which the compound of the formula (II) employed is selected from the group consisting of 2-methylcyclopentanone, 2,2-dimethylcyclopentanone, 2-ethylcyclopentanone, 2,2diethylcyclopentanone, 2-isopropylcyclopentanone, 2-methylcyclohexanone and 2-methylcycloheptanone and the compound of the formula (III) employed is selected from the group consisting of 4-chlorobenzaldehyde, 4-fluorobenzaldehyde, 4-methoxybenzaldehyde, 4-methylbenzaldehyde and 2,4-dichlorobenzaldehyde.

4. The process of claim 1, in which the basic catalyst employed is selected from the group consisting of alkali metal and alkaline earth metal hydroxides and alkali and alkaline earth metal carbonates and oxides of these elements which form hydroxides or carbonates under the reaction conditions.

5. The process of claim 1, in which the reaction medium employed is water without additions of other solvents.

6. The process of claim 1, which is carried out at a temperature from 20° to 200° C. and at a pressure of up to 10 bar.

7. The process of claim 1, in which from 0.5 to 2 mol of the compound of the formula (II) are employed per mole of the compound of the formula (III).

8. The process of claim 1, in which from 0.05 to 0.1 equivalents of catalyst are employed per mole of the compound of the formula (II).

9. The process of claim 1, in which after carrying out the process the reaction mixture obtained is worked up by cooling it, filtering off the solid which is present, washing it with water and drying it.

* * * * *